(12) United States Patent
Kelly et al.

(10) Patent No.: US 6,274,377 B1
(45) Date of Patent: Aug. 14, 2001

(54) INDUCING APOPTOSIS IN A MAMMALIAN CELL BY CONTACTING WITH PARAFFIN OR AGAR

(75) Inventors: Thomas A. Kelly, Norwood, MA (US); Mitchell S. Felder, Sharon; Robert-A Ollar, Milford, both of PA (US)

(73) Assignee: Infectech, Inc., Sharon, PA (US)

( * ) Notice: Subject to any disclaimer, the term of this patent is extended or adjusted under 35 U.S.C. 154(b) by 0 days.

(21) Appl. No.: 09/089,586

(22) Filed: Jun. 3, 1998

(51) Int. Cl.[7] .................................................... C12N 5/00
(52) U.S. Cl. ................................................................ 435/375
(58) Field of Search .............................................. 435/375

(56) References Cited

FOREIGN PATENT DOCUMENTS 030 106  *  6/1981  (EP) .

OTHER PUBLICATIONS

Zhang et al., "Studies on the Reduction of Malignant Phenotypes in a Highly Metastatic Human Lung Carcinoma—Correlated Changes of Intercellular Communication, Cytoskeletons, Oncogenes and Anti–oncogenes." Chung–Hua Chung Liu Tsa Chih 16 (2) : 88–92 1944.*

Nooter et al., "Constitutive expression of the c–H–ras oncogene inhibits doxorubicin–induced apoptosis and promotes cell survival in a rhabdomyosarcoma cell line", British J. Cancer 71: 556–561 (1995).*

Sigounal et al., "dl–alpha–Tocopherol Induces Apoptosis in Erythroleukemia, Prostate, and Breast Cancer Cells", Nutrition and Cancer 28 (1) : 30–35 (1997).*

Bradley et al., "Growth of Mammalian Cells on Carbon–Coated Plastic Substrata", Biochemical Soc. Trans. 18 (5) : 1017 (1990).*

Laluppa et al., "Culture materials affect ex vivo expansion of hematopoietic progenitor cells", J. Biomed. Materials Res. 36 (3):347–359 (1997).*

Re et al., "Inhibition of Anchorage–dependent Cell Spreading Triggers Apoptosis in Cultured Human Endothelial Cells", J. Cell Biology 127 : 537–46 (1994).*

Bentley et al., "Fibronectin Binding Properties of Bacteriologic petri Plates and Tissue Culture Dishes", J. Biomedical Materials Res. 19 : 757–769 (1985).*

Merck Index, Eleventh Edition, entry 6971 (1989).*

W. S. Ramsey et al., Surface Treatments and Cell Attachment, 1984, pp. 802–808.

Martin Lavin et al., Defining Characteristics of Apoptosis and Comparison With Necrosis, *Programmed Cell Death*, 1993, pp. 2–3, Harwood Academic Publishers GmbH.

G. P. Studzinski, *Cell Growth and Apoptosis*, 1995, pp. 123, 125, 140, 153–155, 165, Oxford University Press.

Donald E. Ingber, The Architecture of Life, *Scientific American*, Jan. 1998, pp. 48–57.

* cited by examiner

*Primary Examiner*—Sandra E. Saucier
(74) *Attorney, Agent, or Firm*—David V. Radack; Diane R. Meyers; Eckert Seamans Cherin & Mellott, LLC

(57) ABSTRACT

A method of inducing apoptosis in a cell. The method includes providing an impenetrable and nonmetabolizable material, such as paraffin or agar, and introducing the cell into a contacting relationship with the material. The method also includes providing a substrate and coating the substrate with the impenetrable and nonmetabolizable material.

14 Claims, 15 Drawing Sheets

(14 of 15 Drawing Sheet(s) Filed in Color)

INDUCING APOPTOSIS IN A MAMMALIAN CELL BY CONTACTING WITH PARAFFIN OR AGAR

BACKGROUND OF THE INVENTION

This invention relates to methods of inducing apoptosis in a cell.

Apoptosis, also known as programmed cell death, is characterized by nuclear condensation, fragmentation of DNA and cell shrinkage. Apoptosis is to be contrasted with cell necrosis, which occurs when cells swell, burst and release constituents. Necrosis is usually a cell's response to gross injury. Apoptosis, on the other hand, does not usually result in swelling of the cell, and thus does not cause inflammation and pain. For this reason, cancer researchers are quite interested in inducing apoptosis in cancer cells, as opposed to using other methods (such as chemotherapy) of destroying these cells which can involve terrible side effects.

Therefore, there is a need for a simple and efficient method of inducing apoptosis in a cell. These methods could provide the launching platform for further research into the mechanism and biochemistry of apoptosis to assist researchers in finding better and less painful methods of killing cancer cells.

SUMMARY OF THE INVENTION

The invention herein is a method of inducing apoptosis in a cell. The method comprises providing an impenetrable and nonmetabolizable material, such as paraffin or agar, and introducing the cell into a contacting relationship with the material. The method further includes providing a substrate and coating the substrate with the impenetrable and nonmetabolizable material.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

A full understanding of the invention can be gained from the following detailed description of the invention when read in conjunction with the accompanying drawings in which.

DETAILED DESCRIPTION

Figure 1A:
FIGS. 1A–1L show photos of the various cells (MRC-5, RD and A549) observed under a microscope showing the effect of cell contact with paraffin.

It has been found, quite surprisingly and unexpectedly, that contacting cells, in vitro, to an impenetrable and nonmetabolizable material, such as paraffin and agar, results in apoptosis of the cell. The cells must contact a sufficient amount of the impenetrable and nonmetabolizable material in order to induce apoptosis. While not being limited to a particular explanation, it is believed that cells that contact an impenetrable and nonmetabolizable material cannot spread out flat, and thus, because of this, will not divide. Eventually, the round cells activate a "death program" (apoptosis) and merely ball-up and die. As opposed to necrosis, there is no swelling, but instead the apoptotic cell merely balls-up, shrinks and shrivels away.

As used herein, the term "impenetrable" means a material through which a cell or cells is unable to pass.

As used herein, the term "nonmetabolizable" means a substance that cannot be consumed and assimilated by a cell.

Preferably, the material is a hydrocarbon which is solid at temperatures below about 120° F.

It has been found that contact between the cell and an impenetrable and nonmetabolizable substance will somewhat quickly trigger the "death program" of apoptosis. We have found that apoptosis can occur in minutes upon such contact, although, as will be discussed below, the examples use a logistical minimum of 2.5 hours in order to allow for the fixing and staining (or other preparation procedures) of the cells.

The following examples illustrate the inducing of apoptosis in various types of cells by having contact between the cell and an impenetrable and nonmetabolizable substance.

EXAMPLE 1

Three (3) six-cell (about 8 cc/cell) polystyrene culture plates (Falcon #3046 made by Fisher Scientific) (hereinafter "Plate A", "Plate B" and "Plate C") were provided. In each of the Plates A, B and C, two of the wells were uncoated and two of the wells were coated with about 2 cc of paraffin (Tissue Prep 2 made by Fisher Scientific). The two other wells were not used. The two uncoated wells were "cell control" wells into which 4 cc of media containing about 400K cells were placed. The same amount of media containing about 400K cells were placed into each of the two paraffin coated wells. Plate A contained human fetal lung cells MRC-5 (ATCC No. CCL-171); Plate B contained human lung carcinoma A549 (ATCC No. CCL-185); and Plate C contained human rhabdomyosarcoma RD (ATCC No. CCL-136).

The media containing MRC-5 cells was made as follows. The MRC-5 cells (obtained from Bio Whittaker, Walkersville, Md) were initially grown on 75 cm flasks in Eagle's Minimum Essential Media w/25 mM Hepes without glutamine. To this media was added 5 cc on Pen-Strep Mixture (10000 $\mu$ penicillin and 10000 mg streptomycin) and 5 cc of L-Glutamine 200 mM and 50 cc of heat activated Fetal Calf Serum. Once this media was obtained, trypsan was introduced thereto in order to float the cells. The desired 4 cc aliquots (containing about 400K cells) were then placed in the two uncoated and the two coated wells of Plate A.

The media containing the A549 cells was made similarly except L-15 media was required. Again, the desired 4 cc aliquots (containing about 400K cells) were then placed in the two uncoated and two coated wells of Plate B.

The media containing the RD cells was made in the exact same manner as the media containing the MRC-5 cells. The desired 4 cc aliquots (containing about 400K cells) were then placed in the two uncoated and two coated wells of Plate C.

Figure 1B:
Figure 1C:
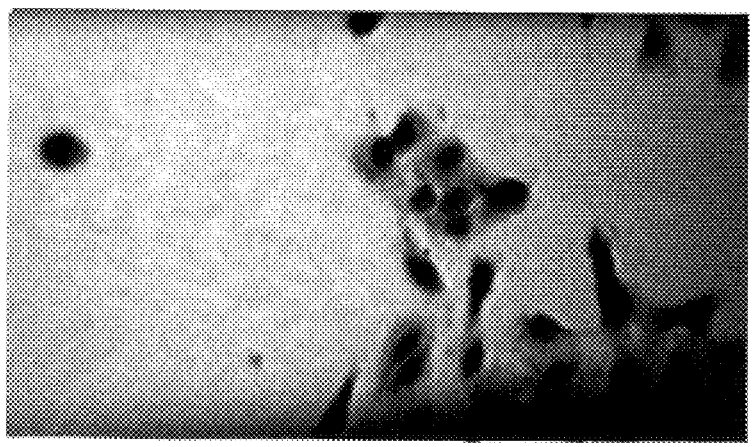

Plates A, B and C were then placed overnight in an incubator at 37° C. having a 6% $CO_2$ environment. After overnight incubation, the excess media was poured off and the cells were fixed with methanol and stained with Giemsa. The plates were then observed by a light microscope. Photographs of the television screen are shown in FIGS. 1A–1L. FIGS. 1A, 1B and 1C show (at 100×) a portion of the MRC-5, RD and A549 cells, respectively, which are present on the uncoated cell culture wells. As can be seen, the pictures show live, viable cells, as would be expected.

Figure 1D:
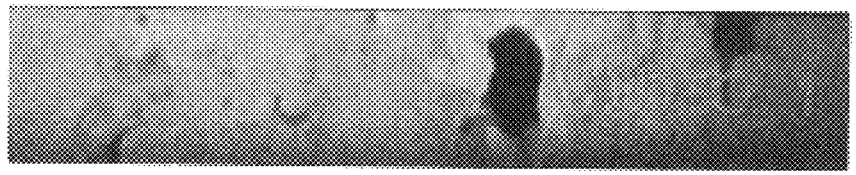
Figure 1E:
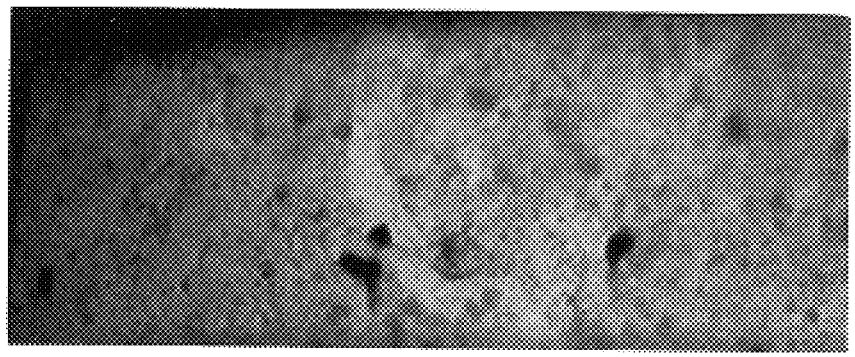
Figure 1F:
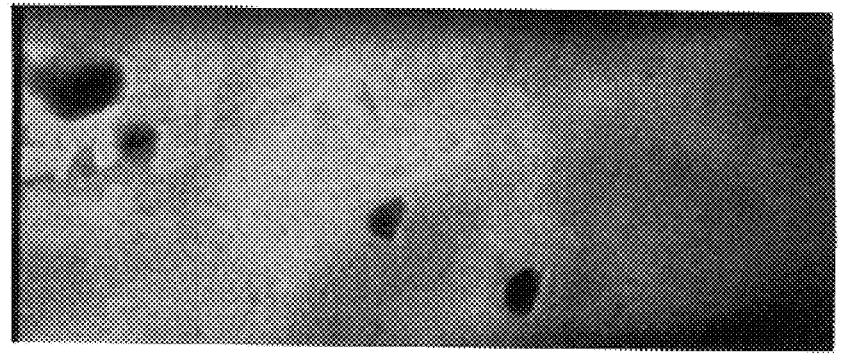

Turning to FIGS. 1D, 1E and 1F, these are pictures of a portion of the MRC-5, RD and A549 cells, respectively, which contacted the paraffin coated cell culture wells. As can be seen, there is a marked decrease in the number of cells from the corresponding pictures of FIGS. 1A–1C. In addition, there is noticeable clumping of cells and the cells are very dense and lack pseudopodia. Most of the cells shown in FIGS. 1D–1F are dead, showing that cell contact with paraffin induces apoptosis.

Figure 1G:
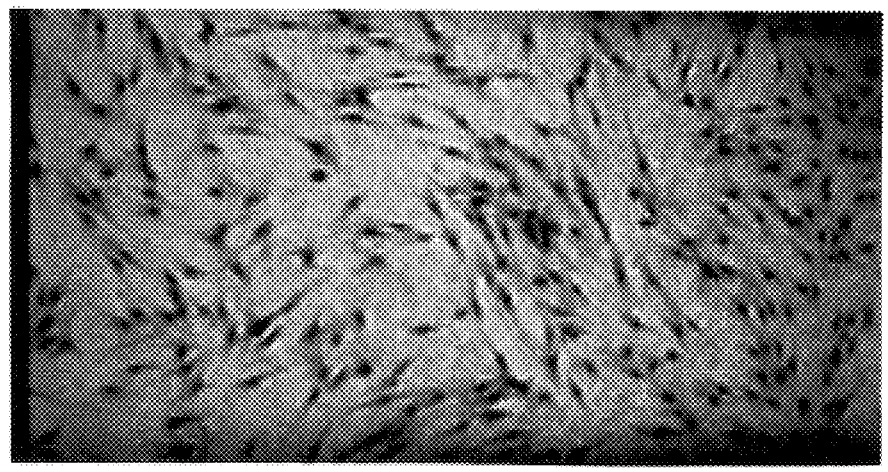
Figure 1H:
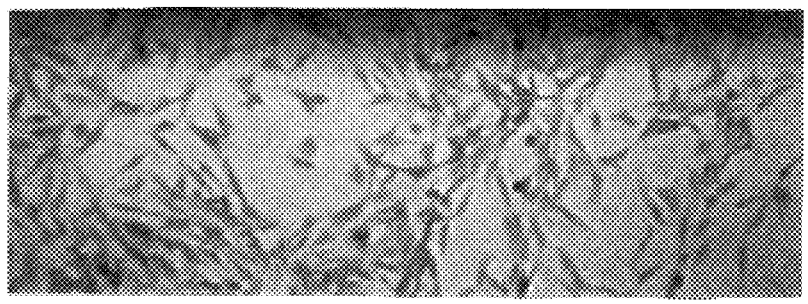
Figure 1I:
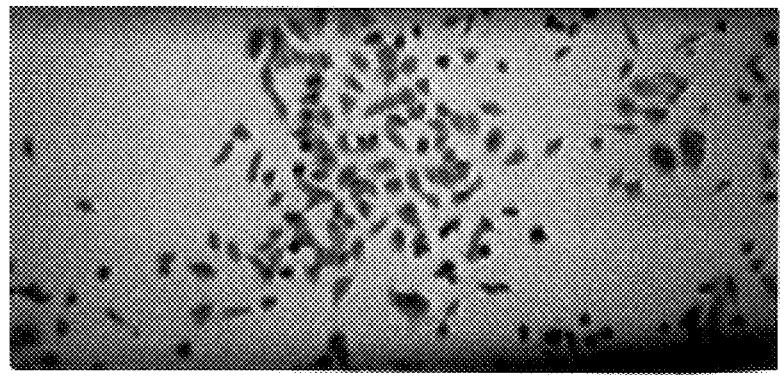
Figure 1J:
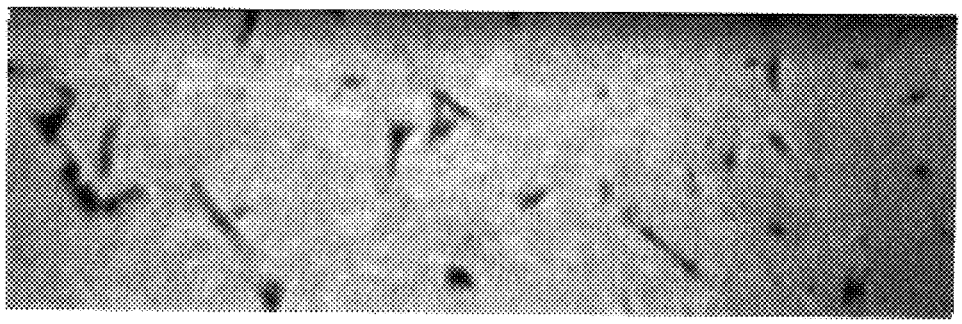
Figure 1K:
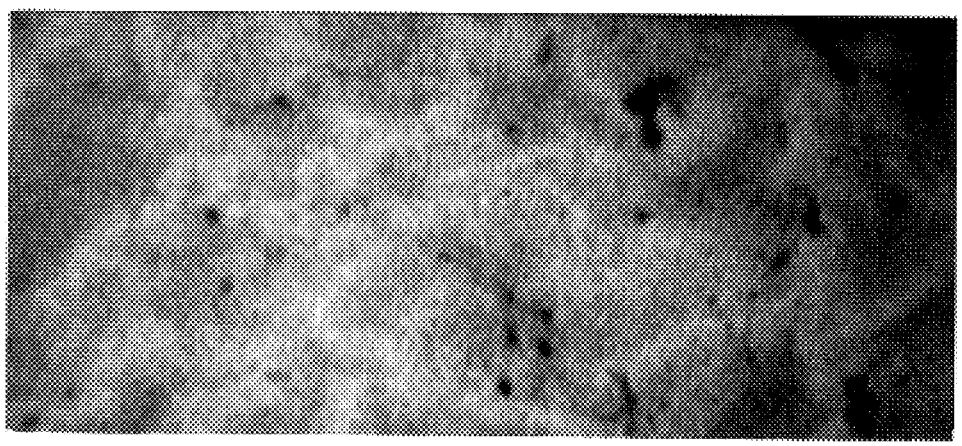
Figure 1L:
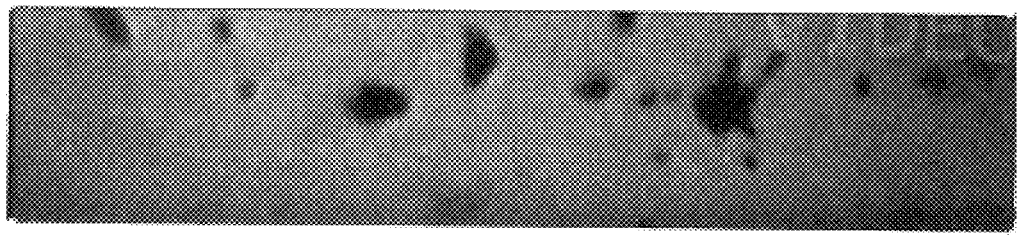

FIGS. 1G–1I show pictures of (at 50×) the same uncoated cell culture wells of the cell controls of MRC-5, RD and A549, respectively, as in FIGS. 1A–1C, after two days. Again, the cells appear viable and live and are present in the expected numbers. FIGS. 1J–1L show pictures of (at 50×) the same cells which have contacted the paraffin coated cell culture wells after two days. It can be seen that there is a marked decrease in the number of cells and those remaining are clumped, dense and lack pseudopodia. These cells are mostly dead, further bolstering the conclusion that cell contact with paraffin induces apoptosis.

Figure 2A:
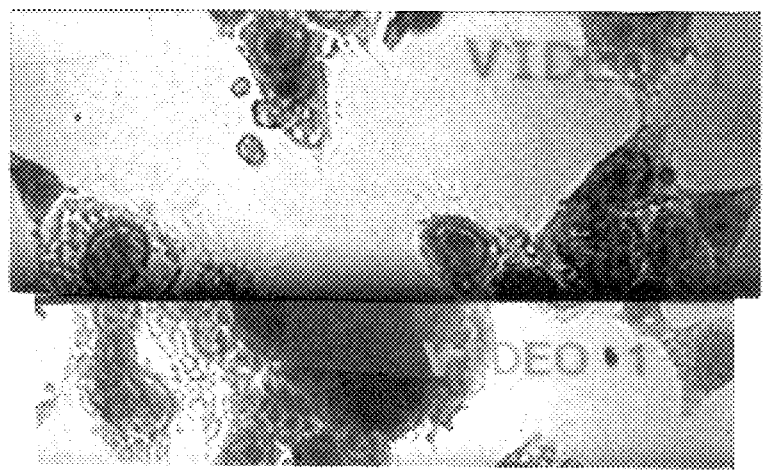
FIGS. 2A–2C show photos of RD cells which have not (FIG. 2A) or have (FIGS. 2B and 2C) been contacted with paraffin.
Figure 2B:
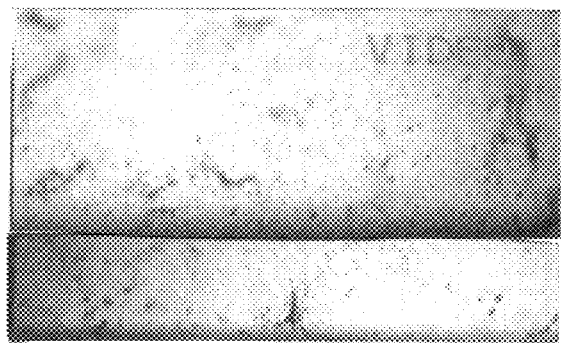
Figure 2C:
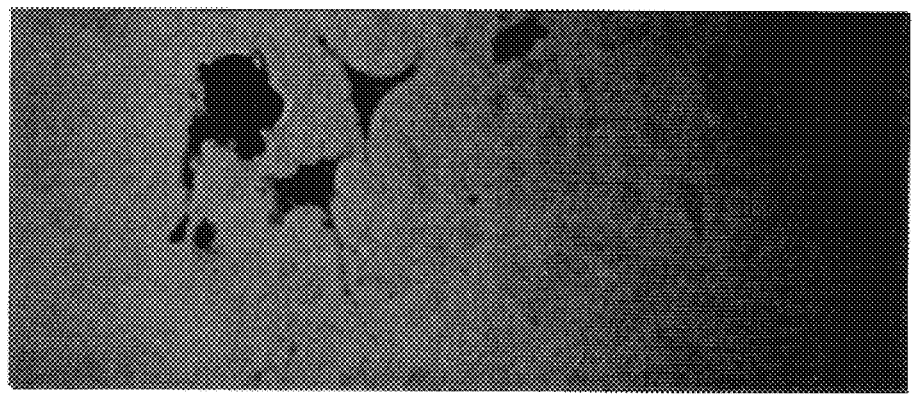

Turning to FIG. 2, FIG. 2A is a composite photo showing the RD cell control (noncoated cell culture well) at 400×. As can be seen, the nucleoli can be seen clearly within the nuclei of the cells and the cells have a refractile appearance, which is a characteristic of a viable RD cell. In comparison, FIG. 2B is a composite photo showing the RD cells which contacted the coated paraffin cell culture wells at 100×. It can be seen that there is hardly any cell growth at all. FIG. 2C shows apoptotic RD cells which were in contact with the paraffin. These cells have dense, atypical nuclei with no recognizable refractility as do healthy RD cells. The apoptotic cells also have a shrunken appearance and stringy pseudopodia, as shown by the arrows in FIG. 2C.

EXAMPLE 2

It was desired to test coatings other than paraffin to see if apoptosis could be induced by other materials. A six-well cell culture plate (Falcon #3046) (hereinafter "Plate D") was provided. This Plate D was not coated with any material and was used as a cell control plate. Media containing MRC-5 cells (as was explained above) was introduced into four of the cell culture wells. Another plate (Falcon #3046) (hereinafter "Plate E") was also provided. Two of the cell culture wells were provided with a thin coating of agar; two of the cell culture wells were provided with a thin coating of petroleum jelly; and the remaining two cell culture wells were provided with a thin coating of olive oil. The thin coating of olive oil was applied by introducing about 1 cc of the olive oil into the well and then wiping the cell culture well with a towel to leave a very thin coating.

After this, 2–4 cc aliquots of media containing about 400K MRC-5 cells were introduced into each cell culture well of Plate E. The aliquots of media containing 400K MRC-5 cells were taken from the same flask as was used in Example 1. Plates D and E were then incubated overnight at 37° C. in a 6% $CO_2$ atmosphere. Again, after incubation, the media was poured off and the cells were fixed with methanol and stained with Giemsa.

Figure 3A:
FIGS. 3A–3C show pictures of MRC-5 cells on agar, petroleum jelly and olive oil, respectively.
Figure 3B:
Figure 3C:

Turning to FIGS. 3A–3C, FIG. 3A shows a picture of the MRC-5 cells on agar from a light microscope at 50×. It will be noted that there is very low cell count and those cells present are dense and apoptotic. In comparison, FIGS. 3B and 3C show pictures of the MRC-5 cells on petroleum jelly and olive oil, respectively. It will be seen that there is an expected (as compared to the cell control culture, not shown) number of cells and these cells are viable and live.

EXAMPLE 3

Figure 3D:
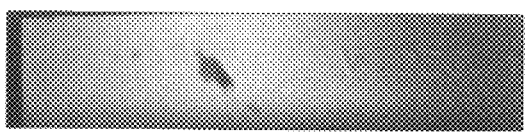
FIGS. 3D–3F show pictures of RD cells on agar, petroleum jelly and olive oil, respectively.
Figure 3E:
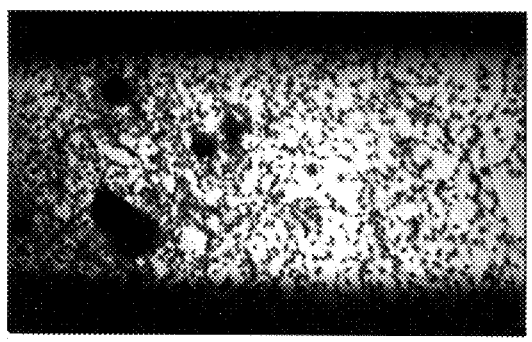
Figure 3F:

A similar experiment as was done above in Example 2 was done in this Example 3 for RD cells. Similar procedures were used in order to obtain the pictures shown in FIGS. 3D–3F. FIG. 3D shows RD cells (or, more to the point, lack thereof) on the agar (50×). The cells present are dense and shrunken. In comparison, the RD cells on petroleum jelly (FIG. 3E) and olive oil (FIG. 3F) are in expected numbers (as compared to the cell control culture, not shown) and are viable and live.

Example 3 shows that, in addition to paraffin, agar also induces apoptosis. Both paraffin and agar are impenetrable and nonmetabolizable, as defined hereinbefore. The petroleum jelly and olive oil, which are penetrable and metabolizable, did not induce apoptosis. It is believed that in the petroleum jelly and olive oil coated wells, pseudopodia of the cells can be extended through the substance and can consume and metabolize the same. Once the cells attach to the polystyrene surface underneath the thin penetrable coating of olive oil or petroleum jelly, cell growth proceeds as normal.

EXAMPLE 4

Figure 4:
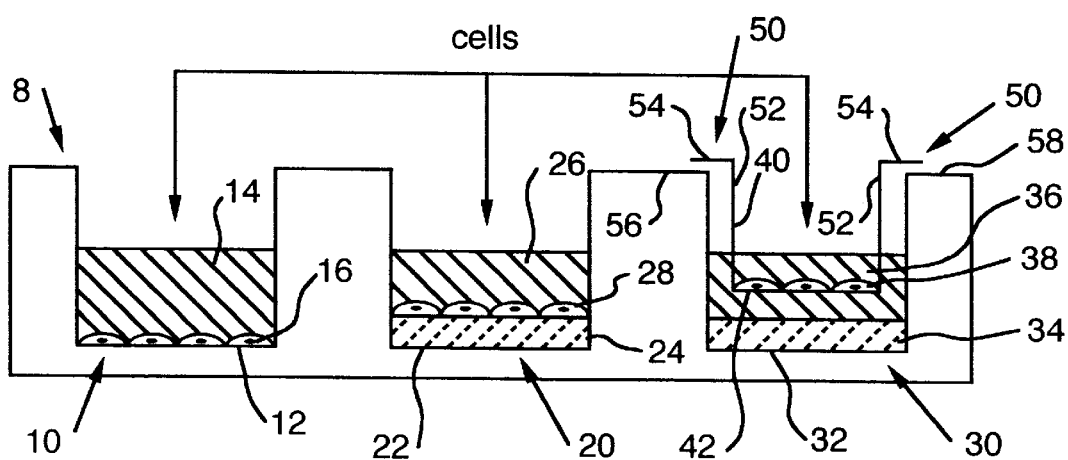
FIG. 4 is a cross-sectional view of a typical cell culture plate.

It was desired to determine further the possible toxicity of paraffin which is in a non-contacting position with the cells. Referring to FIG. 4, a composite cross-sectional diagram of a cell culture plate 8 is shown. In cell culture well 10 the floor 12 of the well 10 is not coated with any material, and the media 14 containing the cells 16 are introduced directly into the well 10. In cell culture 20, the floor 22 is coated with a layer of paraffin 24. The media 26 containing the cells 28 are then introduced directly into the well. Turning to cell culture well 30, the floor 32 again is coated with a layer of paraffin 34. However, before the media 36 containing the cells 38 is introduced therein, a thin filter insert 40 (Falcon #3091 made by Fisher Scientific) is introduced into the well 30. The filter insert 40 has a lower cell support portion 42 and is suspended above the floor 32 of the well 30 by means of a circular flange 50 that has a vertical portion 52 and a horizontal portion 54, with the horizontal portion 54 resting on and supported by land portions 56 and 58 of the cell culture plate 8. As can be seen the filter insert 40 enables the cells 38 to be suspended in the media 36 in a non-contacting relationship with the layer of paraffin 34.

Once again, a cell control plate (hereinafter "Plate F") was provided, which did not contain any coating in the cell culture wells. Into two cell culture wells was introduced media containing MRC-5 cells from the flask mentioned in Example 1. The two other cells were then introduced to media containing RD cells. Another plate, Plate G, had cell culture wells coated with paraffin. A filter insert (such as filter insert 40) was placed into each of four of the cell culture wells. Into two of these cell culture wells, media containing the MRC-5 cells was introduced. Into two other cell culture wells was introduced media containing RD cells. Thus, in all four cell culture wells, the cells were separated from the paraffin coated layer and thus were in a non-contacting relationship.

As before, Plates F and G were incubated at 37° C. in a 6% $CO_2$ atmosphere overnight. After incubation, the media was poured off and the cells fixed and stained by using methanol and Giemsa, respectively.

Figure 5A:
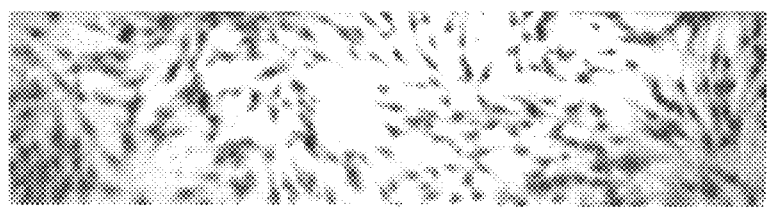
FIGS. 5A–5E show photos of MRC-5 cell control (FIGS. 5A and 5B) and MRC-5 cells grown over the filter insert (FIGS. 5C, 5D and 5E).
Figure 5B:
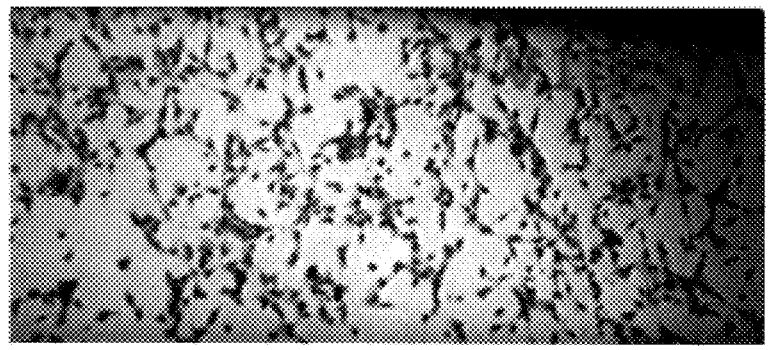

Referring now to FIGS. 5A–5E, FIG. 5A shows a picture (50×) of the MRC-5 cell control from Plate F. As can be seen (and as expected), the cells are numerous and viable. Similarly, FIG. 5B shows a picture (50×) of the RD cell control from Plate F. As can be seen (and as expected), the cells are numerous and viable.

Figure 5C:
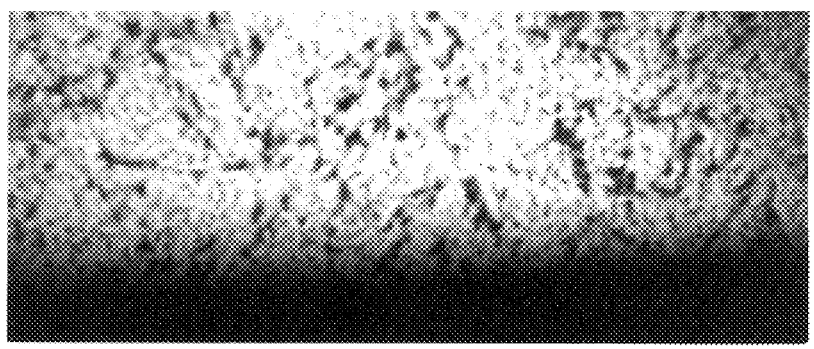
Figure 5D:
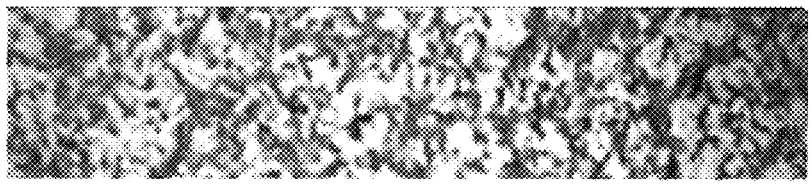
Figure 5E:

FIG. 5C shows a picture (50×) of the MRC-5 cells on the filter insert. As can be seen, the cells appear similar in number as shown in FIG. 5A, and also appear viable and normal. FIGS. 5D (50×) and 5E (100×) show pictures of the RD cells on the filter inserts. Again, thee pictures appear similar to the picture shown in FIG. 5B.

The conclusion that can be drawn from this Example 4 is that contact with paraffin is necessary in order to induce apoptosis and that there is no inherent toxicity of paraffin, as none of the paraffin dissolved into the media to kill the cells.

EXAMPLE 5

It was desired to further show that close contact between the paraffin and the cells was necessary to induce apoptosis. The supernatant fluid containing RD cells which was removed from the cell culture wells of Plate B (Example 1) which were coated with paraffin was reinoculated into two cell culture wells of a new plate (Plate H). These two cell culture wells were not coated with paraffin. The supernatant fluid containing RD cells which was removed from the cell culture wells of Plate B (Example 1) which was not coated with paraffin was reinoculated into one cell culture well of Plate H. Plate H was reincubated for four days.

Figure 6A:
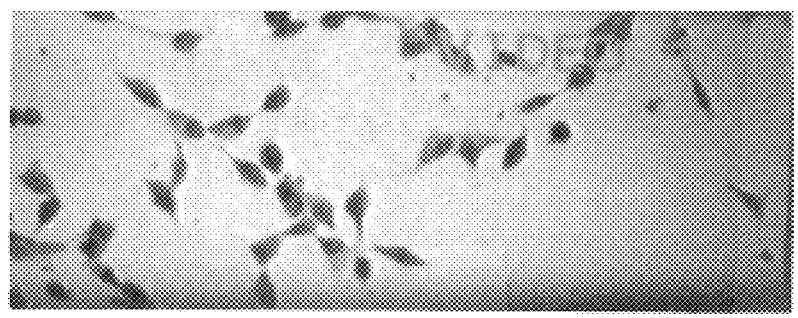
FIGS. 6A–6C show pictures of RD cells recovered from supernatant fluid and reincubated from non-paraffin coated cell control (FIG. 6A) and as recovered from paraffin coated wells (FIGS. 6B and 6C).
Figure 6B:
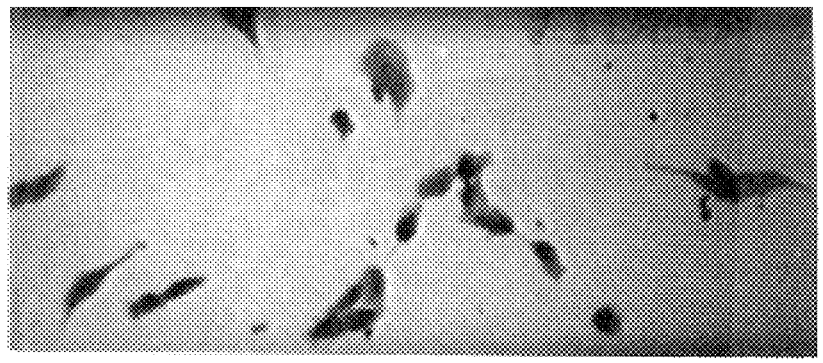
Figure 6C:
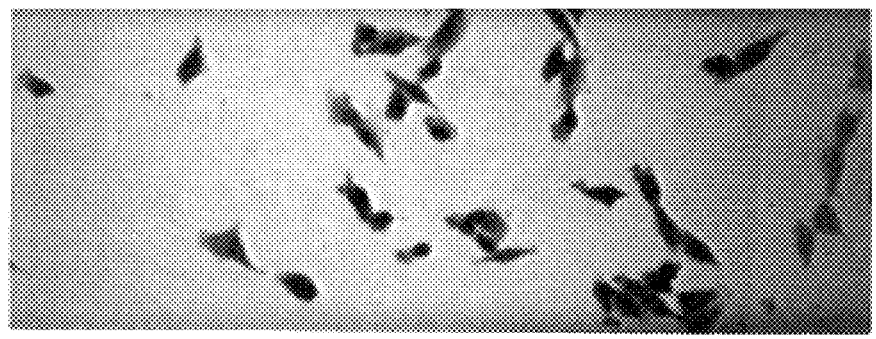

Referring to FIGS. 6A–6C, FIG. 6A shows a picture (100×) of the cell control well in Plate H which was not coated with paraffin. FIGS. 6B and 6C show pictures (100×) of the RD cells in the two (respectively) cell culture wells in Plate H which were coated with paraffin.

As can be seen, FIGS. 6B and 6C, while showing smaller numbers of cells (which is to be expected because many cells died because of contact with the paraffin), viable, normal cells were found attached to the floor of the cell culture well and were dividing.

EXAMPLE 6

It was desired to perform different assays to further confirm apoptosis of the cells which were in contact with the paraffin.

Another six-cell culture plate, Plate I, was prepared, with two cell culture wells having no paraffin coating and two cell culture wells having a paraffin coating on the floor thereof. Media containing RD cells (as was explained above) was introduced into the two uncoated cell culture wells and media containing RD cells was introduced into the two cell culture wells coated with paraffin. Plate I was then incubated for 2.5 hours at 37° C. in a 6% $CO_2$ atmosphere. At this point, rather than fixing and staining the cells, the following protocol was followed:

Step 1: Approximately 3.5 ml of the media containing the RD cells was removed from each of the four wells containing media, leaving 1 ml to cover the floor of each of the four cell culture wells.

Step 2: Add 100 microliters of propidium iodide (PI) working solution.

Step 3: Put Plate I on ice for approximately 30 minutes.

Step 4: Add 1.9 mil of 25% ethanol.

Step 5: Add 50 microliters of benzimidazole dye made by Hoechst (hereinafter HO 342).

Step 6: Again, put on ice for 30 minutes.

Step 7: Remove the fluid.

Step 8: Wash with phosphate buffered saline (PBS).

Step 9: Finally, fix with absolute methanol and rinse with sterile water. Let the Plate I dry.

Plate I was then ready for viewing on the Nikon TE-300 inverted UV/Phase Contrast Microscope.

Figure 7A:
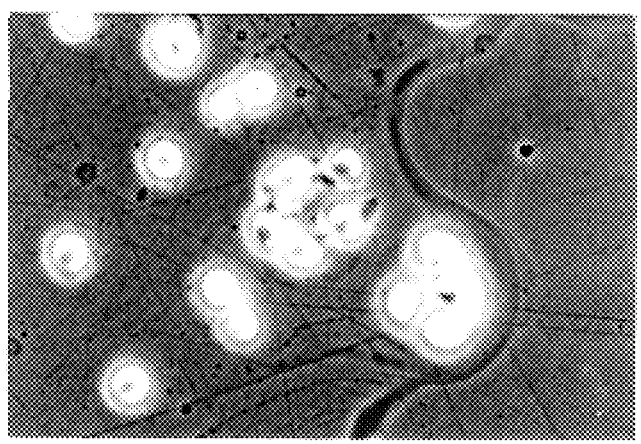
FIGS. 7A–7O show photos of various cells after various apoptosis assays, such as HO 324 and PI tests, have been performed.

FIG. 7A shows a phase contrast view of a portion of the RD cell control culture well (i.e., no paraffin coating). This shows a viable RD cell, in which the nuclei can be clearly seen. The characteristic refractility of viable cell can also be clearly seen.

Figure 7B:
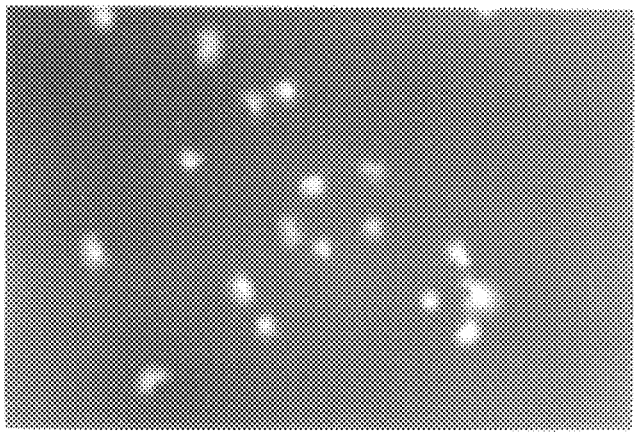

The UV lamp of the microscope is then activated and a filter appropriate for viewing HO 324 is used (i.e., Excitor 330–380 nm; Mirror 400 nm; Emitter LP 420 nm). The same portion as was shown in FIG. 7A is shown in FIG. 7B under UV light. The lightly blue staining shows the DNA of the cells. This shows that the cells are viable as they can pick up the HO 324.

Figure 7C:
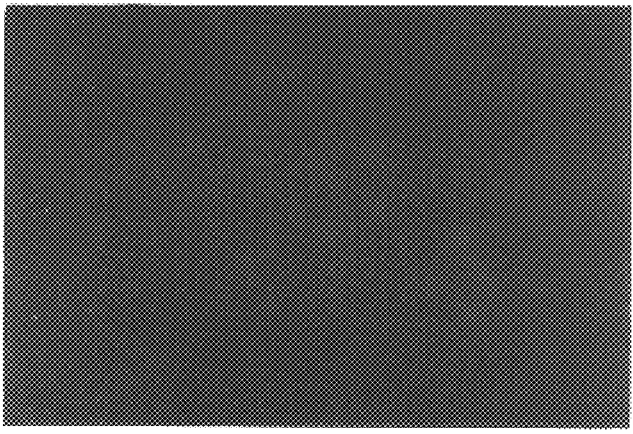

Then, still with UV light, a filter appropriate to detect PI is used (i.e., Excitor 510–560 nm; Mirror 580 nm; Emitter LP 590 nm). As can be seen in FIG. 7C, the cells did not pick up the PI, showing that the cell walls of these cells are not leaky. As is known, if a cell is dead, the walls will become leaky and the PI will be picked up by the cells. As FIG. 7C shows, no PI is picked up by the cells, thus showing that the cells are viable.

Figure 7D:
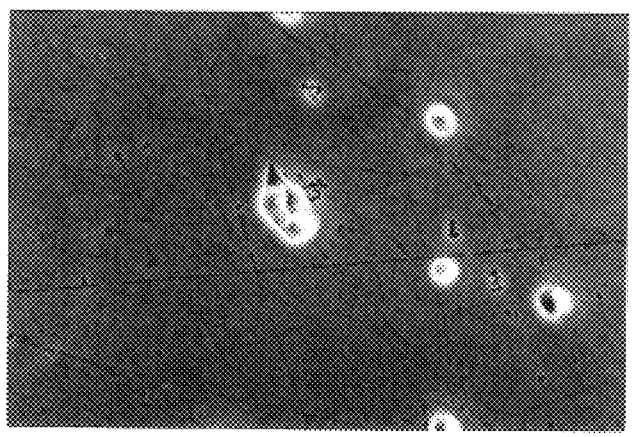
Figure 7E:
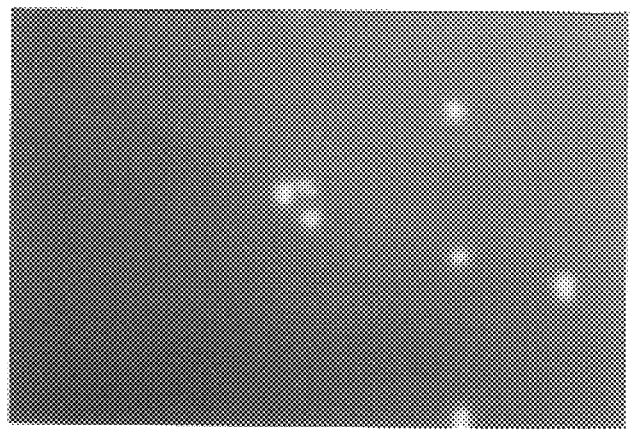
Figure 7F:
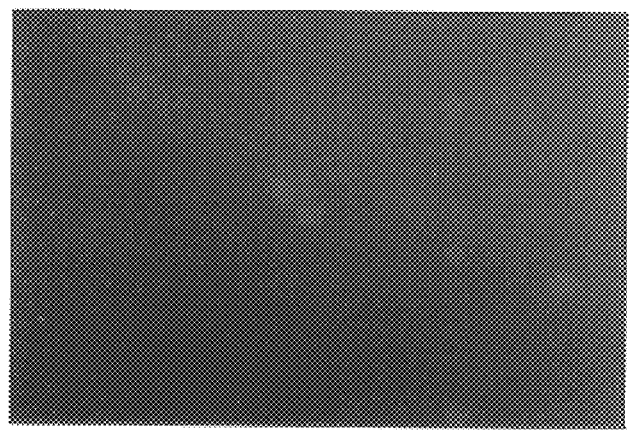

FIGS. 7D–7F show a series of a different portion of the cell culture well used for FIGS. 7A–7C. Again, FIG. 7D shows viable, retractile cells; FIG. 7E shows DNA which picks up HO 324; and FIG. 7F shows that the cells did not pick up PI.

Figure 7G:
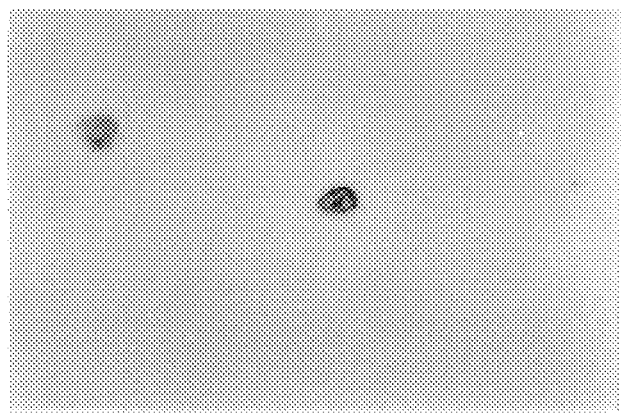
Figure 7H:
Figure 7I:
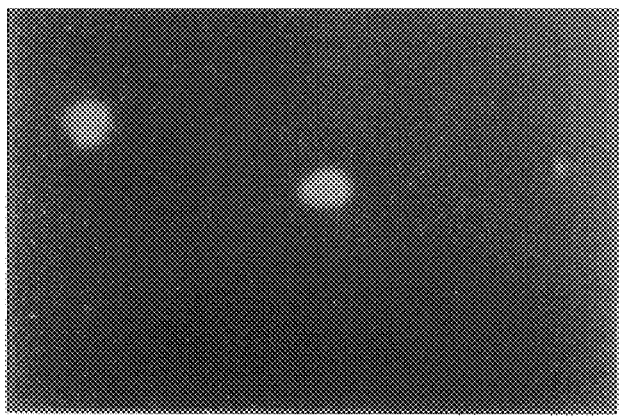

FIGS. 7G–7I show a series of pictures of a portion of the cell culture well coated with paraffin of Plate I. In addition to the almost total lack of cells (a strong indicator of apoptosis, as was discussed above), the remaining cells are definitely apoptotic as shown by the lack of refractility and an observable nucleus as shown in FIG. 7G. Furthermore, FIG. 7H shows the lack of the light blue staining (a white splotch can only be seen) which proves than there is nucleic fragmentation of the DNA and that the DNA is leaking out of the cell and the cell is dying. Simply put, the HO 324 is not being held and thus the cell has undergone apoptosis. Finally, FIG. 7I shows the characteristic bright red spots which indicate that the cell has taken up PI, indicating that the cell wall is leaky.

Figure 7J:
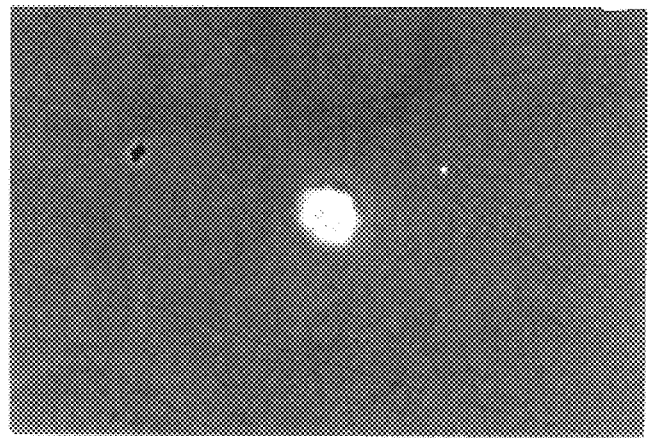
Figure 7K:
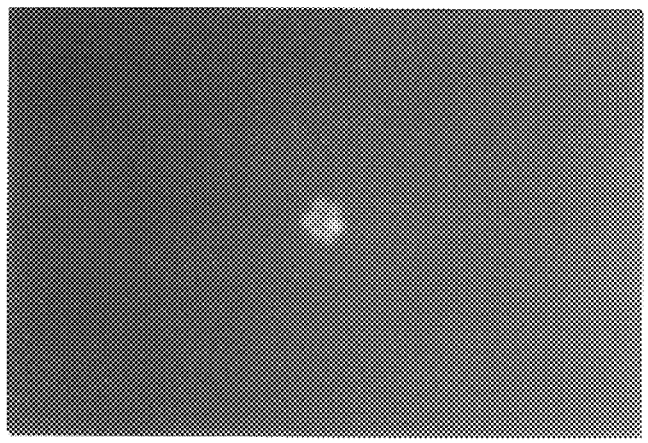
Figure 7L:
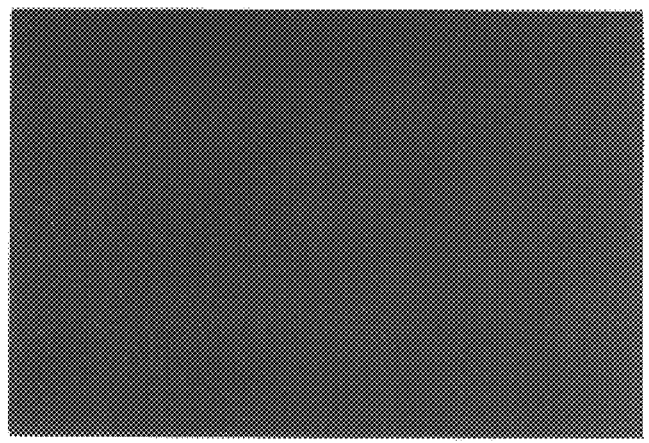

Yet another plate, Plate J, was prepared in a similar way to Plate I, only this time media containing MCF-7 cells were introduced into the four cell culture wells. FIGS. 7J–7L show viable MCF-7 cells (note there are less cells because MCF-7 cells are slow growers) by indicating refractility (FIG. 7J); picking up HO 324 (FIG. 7K); and not picking up PI (FIG. 7L).

Figure 7M:
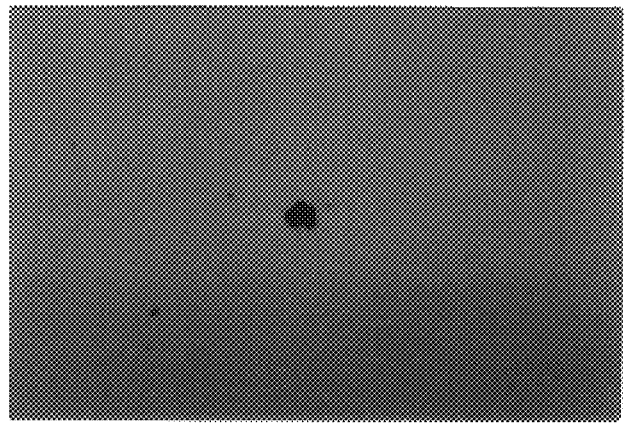
Figure 7N:
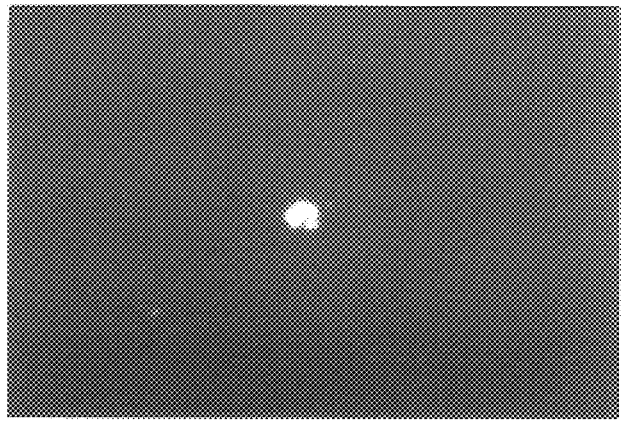
Figure 7O:

FIGS. 7M, 7N and 7O show a series of pictures of the cell culture well coated with paraffin at Plate J. In addition to the almost total lack of cells (a strong indicator of apoptosis) the remaining cells are definitely apoptotic as shown in FIG.

7M. Furthermore, FIG. 7N shows the lack of the light blue staining (a white splotch can only be seen) which proves that there is nucleic fragmentation of the DNA and that the DNA is leaking out of the cell and the cell is dying. Simply put, the HO 324 is not being held and thus the cell has undergone apoptosis. Finally, FIG. 7O shows the characteristic bright red spot which indicates that the cell has taken up PI, indicating that the cell is leaky.

EXAMPLE 7

A traditional trypsan blue viability assay was performed on a cell culture plate, Plate K, containing a cell culture well having no paraffin coating and a cell culture well having a paraffin coating. In this assay, the media containing the MCF-7 cells was introduced into each of the above-mentioned cell culture wells. Plate K was then incubated for 2.5 hours and then the following procedure was followed:
Step 1: Remove all media from the wells.
Step 2: Wash the plate with PBS.
Step 3: Add 0.25% trypsan blue to each well.
Step 4: Let the trypsan stand for 30 seconds to 1 minute.
Step 5: Rinse the plate in sterile water.

Figure 8A:
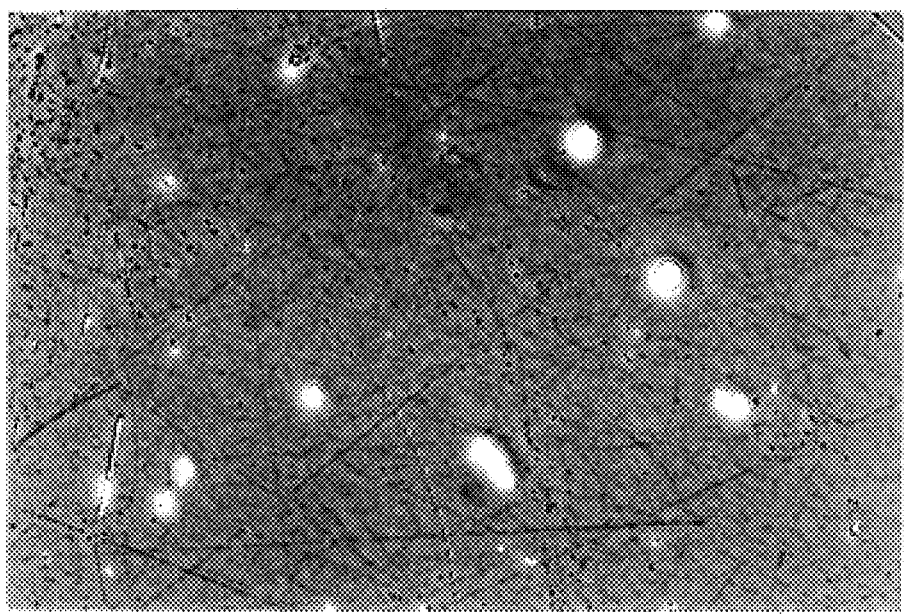
FIGS. 8A and 8B show photos of MCF-7 cells after trypsan blue viability tests have been performed.
Figure 8B:
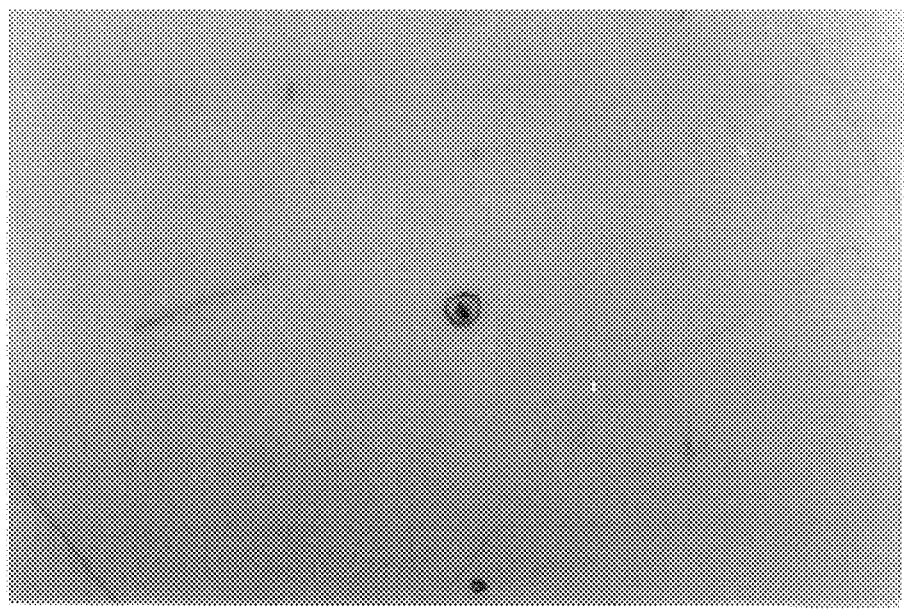

Once Plate K was dried, it was observed under a light microscope. FIG. 8A shows the cell control culture well (i.e., no paraffin coating). The cells have a retractile, viable appearance and did not take up any of the trypsan blue. FIG. 8B, on the other hand, shows a lack of cells (as would be expected as they were in contact with paraffin) and also shows one cell (indicated by the red arrow) that has taken up the trypsan blue and thus is apoptotic.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of inducing apoptosis in a live mammalian cell in vitro comprising:
   providing solidified paraffin; and
   introducing said cell into a contacting relationship with said solidified paraffin; wherein contact between said cell and said solidified paraffin results in apoptosis.

2. The method of claim 1, wherein said material is solid at temperatures below about 120° F.

3. The method of claim 1, wherein said cell is a human fetal lung cell.

4. The method of claim 1, wherein said cell is a human lung carcinoma.

5. The method of claim 1, wherein said cell is a human rhabdomyosarcoma cell.

6. The method of claim 1, wherein said cell is a human breast carcinoma cell.

7. A method of inducing apoptosis in a live mammalian cell in vitro comprising:
   providing a substrate;
   coating at least a portion of said substrate with solidified paraffin; and
   introducing said cell into a contacting relationship with said solidified paraffin; wherein contact between said cell and said solidified paraffin results in apoptosis.

8. The method of claim 7, wherein said substrate is made of polystyrene.

9. The method of claim 7, wherein said material is solid at temperatures below about 120° F.

10. The method of claim 7, wherein said cell is a human fetal lung cell.

11. The method of claim 7, wherein said cell is a human lung carcinoma.

12. The method of claim 7, wherein said cell is a human rhabdomyosarcoma cell.

13. The method of claim 7, wherein said cell is a human breast carcinoma cell.

14. A method of inducing apoptosis in a live mammalian cell, in vitro, comprising:
   providing agar that is impenetrable and nonmetabolizable; and
   introducing said cell into a contacting relationship with said agar; wherein contact between said cell and said agar results in apoptosis.

* * * * *